United States Patent [19]

Demus et al.

[11] 4,363,767
[45] Dec. 14, 1982

[54] ESTERS OF 4-[2,2-DICYANO-ETHENYL]-PHENOLS

[75] Inventors: Dietrich Demus, Halle; Wolfgang Weissflog, Halle-Neustadt; Horst Zaschke, Halle; Rudolf Wolff, Halle; Horst Kresse, Halle, all of German Democratic Rep.

[73] Assignee: VEB Werk für Fernsehelektronik Berlin im VEB Kombinat Mikroelektronik, Berlin, German Democratic Rep.

[21] Appl. No.: 202,958

[22] Filed: Oct. 3, 1980

[30] Foreign Application Priority Data

Jan. 11, 1980 [DD] German Democratic Rep. ... 218410
Jan. 11, 1980 [DD] German Democratic Rep. ... 218411

[51] Int. Cl.³ .................. C07C 121/70; C09K 3/34
[52] U.S. Cl. .................. 260/463; 260/465 D; 252/299.63; 252/299.67
[58] Field of Search .......... 260/465 D, 463; 252/299.61–299.68

[56] References Cited

U.S. PATENT DOCUMENTS 4,147,655 4/1979 Dubois et al. .................. 252/299

Primary Examiner—Dolph H. Torrence
Attorney, Agent, or Firm—Jordan and Hamburg

[57] ABSTRACT

The invention relates to liquid-crystalline nematic mixtures which are used in electro-optical components, as well as to methods for their preparation.

The object of the invention is liquid-crystalline mixtures for electro-optical arrangements possessing high positive electrical anisotropy at a high clarification point, as well as methods for their preparation.

According to the invention, liquid-crystalline nematic mixtures are used, wherein at least one component is a 1,4-disubstituted benzene derivative and the other compound is an ester of 4-[2,2-dicyano-ethenyl]-phenol of the general formula

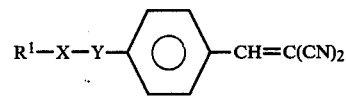

wherein $R^1$ denotes added groups of various characters such as alkyl or alkoxy for example, X is aromatic, cycloaliphatic or a heterocyclic ring system such as phenyl or cyclohexyl for example; and Y is a connector such as carbonyloxy, azomethine, azoxy.

These are prepared by reaction with reactive acid derivatives, particularly acid chlorides, or by a Knoevenagel-condensation by reacting respective 4-subst.-benzoic acid-[4-formyl-phenyl esters] or 4-alkyl-cyclohexanecarboxylic acid-[4-formyl-phenyl esters] with malonic acid dinitrile.

12 Claims, No Drawings

ESTERS OF 4-[2,2-DICYANO-ETHENYL]-PHENOLS

BACKGROUND OF THE INVENTION

The invention relates to liquid-crystalline nematic mixtures functioning in electro-optical arrangements to modulate transmitted or incident light as well as to reproduce numbers, signs and images, and to methods for their preparation.

It is known that electro-optical arrangements for the modulation of light may be produced with the aid of appropriate nematic liquid-crystalline substances and that the same substances also serve to reproduce numbers, signs and images. Nematic liquid crystal with positive dielectrical anisotropy especially allow for the construction of rotary cells or cells based upon the guest-host effect (M. Tobias, International Handbook of Liquid Crystal Displays 1975-1976, Ovum Ltd. London 1976).

Substances of high positive dielectrical anisotropy are needed in order to obtain low swelling and working potentials, particularly advantageous with battery activated devices. The melting and clarification points of the substances used are also extremely important because they determine the range of operating temperature of the components. Due to the fact that there are no substances presently known which possess the combination of the relatively high clarification point required and also of a sufficiently low melting point, mixtures are exclusively used where lowering of the melting point of multi-component systems is utilized. In order to be able to accommodate the mixtures to various requirements, suitable substances are needed as components and a constant search is carried on for new appropriate compounds.

The object of the invention is liquid-crystalline compounds having high positive dielectrical anisotropy and high clarification points, as well as methods for their preparation.

SUMMARY OF THE INVENTION

The task is fulfilled according to the invention by mixing the compounds illustrated below with other liquid crystalline compounds or non-liquid crystalline compounds as components of such liquid-crystalline mixtures for the modulation of incident or transmitted light as well as for the reproduction of numbers, signs and images. The general formula is $R^1$—X—Y—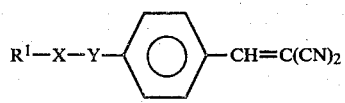—CH=C(CN)$_2$ wherein X =

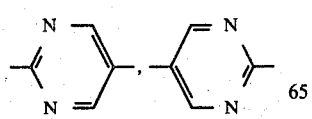

and $R^1 = C_nH_{2n+1}$, Y = —COO— or X =

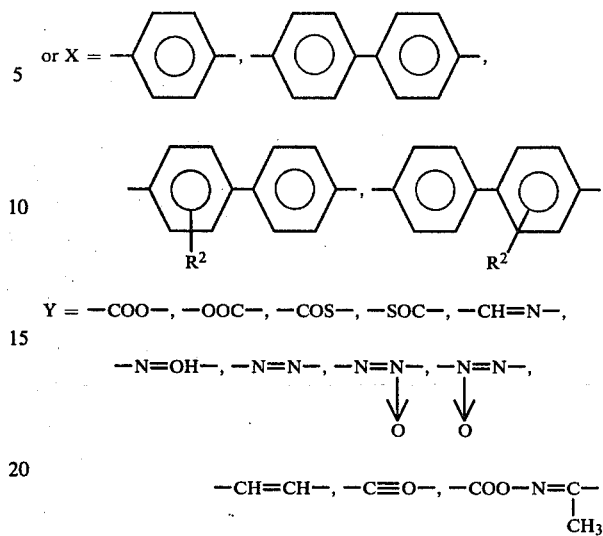

Y = —COO—, —OOC—, —COS—, —SOC—, —CH=N—,

—N=OH—, —N=N—, —N=N—↓O, —N=N—↓O,

—CH=CH—, —C≡O—, —COO—N=C—|CH$_3$ $R^1 = C_nH_{2n+1}$, $C_nH_{2n+1}O$, $C_nH_{2n+1}S$, $C_nH_{2n+1}COO$, $C_nH_{2n+1}O\,COO$, $C_nH_{2n+1}NH$, $C_nH_{2n+1}(CH_3)N$ $R^2$ = F, Cl, Br, CH$_3$, C$_2$H$_5$, CH$_3$O with n = all numbers between 1 and 10, respectively.

The advantages of the mixtures according to the invention are that they are stable and colorless, and have high positive dielectrical anisotropy and high clarification points.

According to the invention the new liquid-crystalline ester of 4-[2,2-dicyano-ethenyl]-phenol are prepared by the reaction with reactive acid derivatives, particularly acid chlorides, of the general scheme

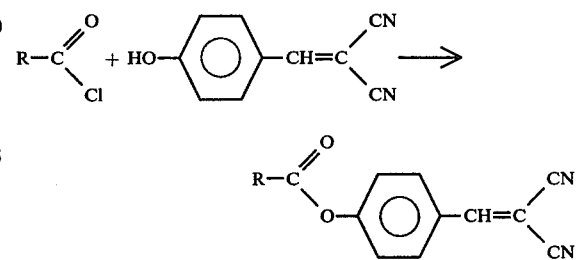

or by a Knoevenagel-reaction of respective 4-subst.-benzoic acid-[4-formyl-phenyl esters] or 4-alkyl-cyclohexanecarboxylic acid-[4-formyl-phenyl esters] with malonic acid dinitrile according to the general scheme:

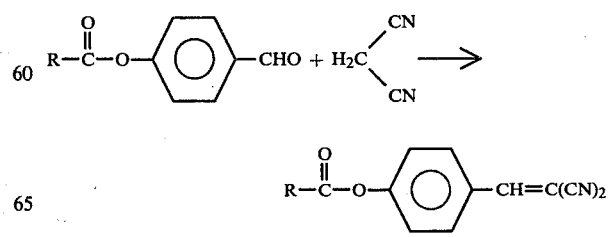

The method provides reproducable high yields.

DETAILED DESCRIPTION OF PREFERRED EMBODIMENTS

The invention is explained with the aid of six examples:

EXAMPLE 1

The following table illustrates compounds which function as components of the mixtures according to the invention along with their melting points and their clarification points. Here denote K=crystalline solid, N=nematic, $S_A$=smectic, I=isotropic-liquid. Number in parentheses denote monotropic liquid-crystalline phases.

$$R^1-X-\overset{\overset{O}{\|}}{C}O-\bigcirc-CH=C(CN)_2$$

| No. | $R^1$ | X | K | $S_A$ | N | I |
|---|---|---|---|---|---|---|
| 1 | $C_6H_{13}$ | –⌬– | . 88.5 | — | (. 54) | . |
| 2 | $C_4H_9O$ | –⌬– | . 132 | — | (. 97) | . |
| 3 | $C_5H_{11}O$ | –⌬– | . 131 | — | (. 89.5) | . |
| 4 | $C_6H_{13}O$ | –⌬– | . 98 | — | (. 94.5) | . |
| 5 | $C_9H_{19}O$ | –⌬– | . 84 | . 90 | . 96 | . |
| 6 | $C_4H_9COO$ | –⌬– | . 111 | — | (. 101) | . |
| 7 | $C_6H_{13}COO$ | –⌬– | . 84 | — | . 102 | . |
| 8 | $C_6H_{13}OCOO$ | –⌬– | . 95.5 | — | (. 95) | . |
| 9 | $C_2H_5$ | –⌬(H)– | . 75 | — | (. 47) | . |
| 10 | $C_6H_{13}$ | –⌬(H)– | . 75 | . 79 | (. 86) | . |

EXAMPLE 2

The static dielectric anisotropies are:
Substance #5= +7 at 363° K. (90° C., 194° F.)
Substance #7= +9.5 at 353° K. (80° C., 176° F.)

EXAMPLE 3

The components of the mixtures according to the invention possess high values of positive dielectrical anisotropy at low frequencies as well as in the static dielectrical range, due to a relaxation process and the concomitant loss of the longitudinal components of the dipole moment at higher frequencies but negative dielectrical anisotropy ($\Delta\Sigma < 0$). For this reason, these substances are suited for displays, based upon the two-frequency process. Substance #7 possesses a relaxation range at the following frequencies;

| Frequency (MHz) | Temperature (°C.) |
|---|---|
| 0.89 | 81 |
| 1.47 | 89.5 |
| 2.20 | 96 |

EXAMPLE 4

The basic mixture "Mi 8" consists of the following components:

|  | mol % |
|---|---|
| methoxybenzoic acid hexyloxyphenyl ester | 19.6 |
| pentyloxybenzoic acid octyloxyphenyl ester | 29.5 |
| hexylbenzoic acid butyloxyphenyl ester | 29.5 |
| butyloxycarbonyloxybenzoic acid hexyloxyphenyl ester | 11.8 |
| 2-ethylhydroquinone-bis-[4-n-hexylbenzoate] | 9.5 |

A mixture of 90% by weight Mi 8 and 10% by weight of

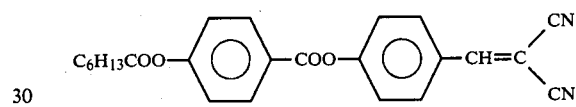

has a clarification point at 71.5° C. This mixture does not exhibit any crystallization after one week at −10° C. The swelling potential of the dielectrical rearrangement in a twist cell amounts to 3.7 Volts (thickness of layer: 20 μm, frequency: 500 Hz).

EXAMPLE 5

The esters of 4-[2,2-dicyano-ethenyl]-phenol according to the first variant are prepared as follows:

2.7 g (0.01 mol) 4-n-hexylcarbonyloxy-benzoyl chloride are added to 1.7 g (0.01 mol) 4-[2,2-dicyano-ethenyl]-phenol dissolved in 15 ml absolute pyridine. The mixture is stirred and left standing at room temperature. After 24 hours, the mixture is poured upon 200 g ice and 20 ml conc. sulfuric acid, and the precipitated ester is sucked off and thoroughly washed with water. The ester is purified by three recrystalizations from methanol. The yield amounts to 90% of theoretical. The conversion temperatures are:

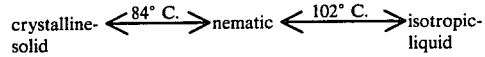

The other esters are prepared by analogous methods by substituting the respective acid chloride (0.01 mol) for the 4-n-hexylcarbonyloxy-benzoyl chloride.

EXAMPLE 6

The esters of 4-[2,2-dicyano-ethenyl]-phenol are prepared according to the Knoevenagel condensation as follows: 3.3 g (0.01 mol) 4-n-hexyloxybenzoic acid [4-formyl-phenyl ester] and 0.66 g (0.01 mol) malonic acid dinitrile are dissolved in 40 ml abs. ethanol, and after addition of 5 drops of piperidine, heated three minutes to boiling at reflux. After cooling, the precipitate is sucked off and recrystallized from ethanol. The yield amounts to 85% of the theoretical value. The conversion temperatures are:

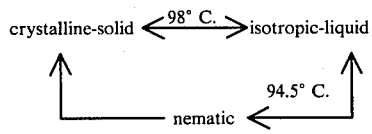

The other compounds are prepared by analogous procedures, replacing the 4-n-hexyloxybenzoic acid [4-formyl-phenyl ester] by the respective 4-formyl-phenyl ester of another respective acid (0.01 mol).

We claim:

1. An ester of a 4-(2,2-dicyano-ethenyl)phenol of the formula

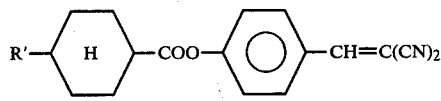

wherein $R^1 = C_2H_5$ or $C_6H_{13}$.

2. An ester of a 4-(2,2-dicyano-ethenyl)phenol of the formula

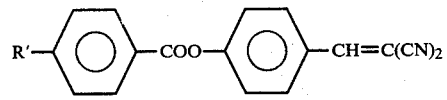

wherein $R^1 = C_6H_{13}$, $C_4H_9O$, $C_5H_{11}O$, $C_6H_{13}O$, $C_9H_{19}O$, $C_4H_9COO$, $C_6H_{13}COO$, or $C_6H_{13}OCOO$.

3. The compound of claim 2 which is a compound of the formula

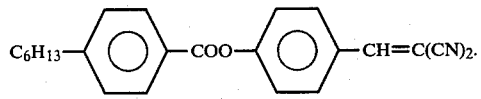

4. The compound of claim 2 which is a compound of the formula

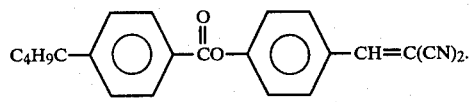

5. The compound of claim 2 which is a compound of the formula

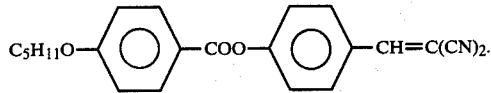

6. The compound of claim 2 which is a compound of the formula

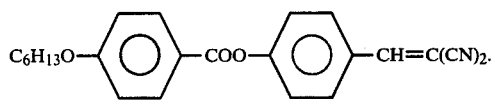

7. The compound of claim 2 which is a compound of the formula

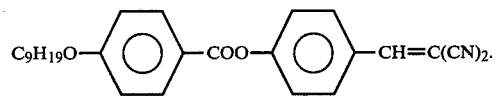

8. The compound of claim 2 which is a compound of the formula

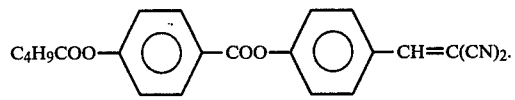

9. The compound of claim 2 which is a compound of the formula

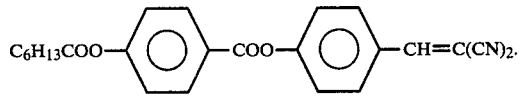

10. The compound of claim 2 which is a compound of the formula

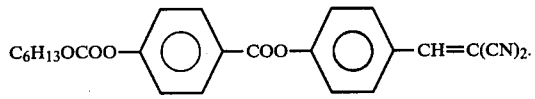

11. The compound of claim 1 which is a compound of the formula

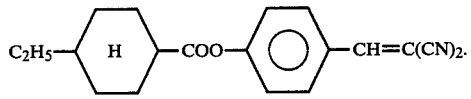

12. The compound of claim 1 which is a compound of the formula

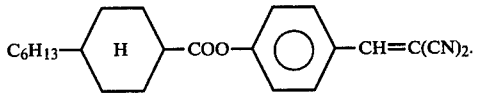

* * * * *